(12) United States Patent
Azapagic

(10) Patent No.: US 10,808,689 B2
(45) Date of Patent: Oct. 20, 2020

(54) PERISTALTIC PUMP HAVING IMPROVED PUMPING FINGERS

(71) Applicant: Curlin Medical Inc., Elma, NY (US)

(72) Inventor: Azur Azapagic, Cottonwood Heights, UT (US)

(73) Assignee: Curlin Medical Inc., Elma, NY (US)

( * ) Notice: Subject to any disclaimer, the term of this patent is extended or adjusted under 35 U.S.C. 154(b) by 39 days.

(21) Appl. No.: 16/222,382

(22) Filed: Dec. 17, 2018

(65) Prior Publication Data

US 2020/0191134 A1   Jun. 18, 2020

(51) Int. Cl.
*F04B 43/12* (2006.01)
*A61M 5/142* (2006.01)

(52) U.S. Cl.
CPC ..... *F04B 43/1246* (2013.01); *A61M 5/14232* (2013.01); *F04B 43/1253* (2013.01); *F04B 43/1276* (2013.01)

(58) Field of Classification Search
CPC ............ A61M 5/14232; F04B 43/1246; F04B 43/1253; F04B 43/1276
USPC ................................................ 417/474, 476
See application file for complete search history.

(56) References Cited

U.S. PATENT DOCUMENTS

| | | |
|---|---|---|
| 4,653,987 A | 3/1987 | Tsuji et al. |
| 5,290,239 A | 3/1994 | Classey et al. |
| 5,575,631 A * | 11/1996 | Jester ................ A61M 5/14228 417/474 |
| 5,683,233 A | 11/1997 | Moubayed et al. |
| 5,791,881 A | 8/1998 | Moubayed et al. |
| 5,924,852 A | 7/1999 | Moubayed et al. |
| 6,371,732 B1 | 4/2002 | Moubayed et al. |
| 2002/0094287 A1 | 7/2002 | Davis |
| 2007/0048161 A1 | 3/2007 | Moubayed |

* cited by examiner

*Primary Examiner* — Connor J Tremarche
(74) *Attorney, Agent, or Firm* — Hodgson Russ LLP

(57) ABSTRACT

A pumping finger subassembly for a peristaltic infusion pump has a housing, a pinch member, a block member, and at least one biasing spring. The housing includes a transverse slot, a first side wall, and an open second side through which the pinch member and biasing spring(s) are inserted into the transverse slot. The block member includes a foot portion and a side wall portion. The foot portion is insertable into the housing through the open second side such that the block member is constrained against movement relative to the housing and the side wall portion of the block member opposes the first side wall of the housing, whereby the pinch member is supported on both lateral sides to prevent tilting of the pinch member.

8 Claims, 4 Drawing Sheets

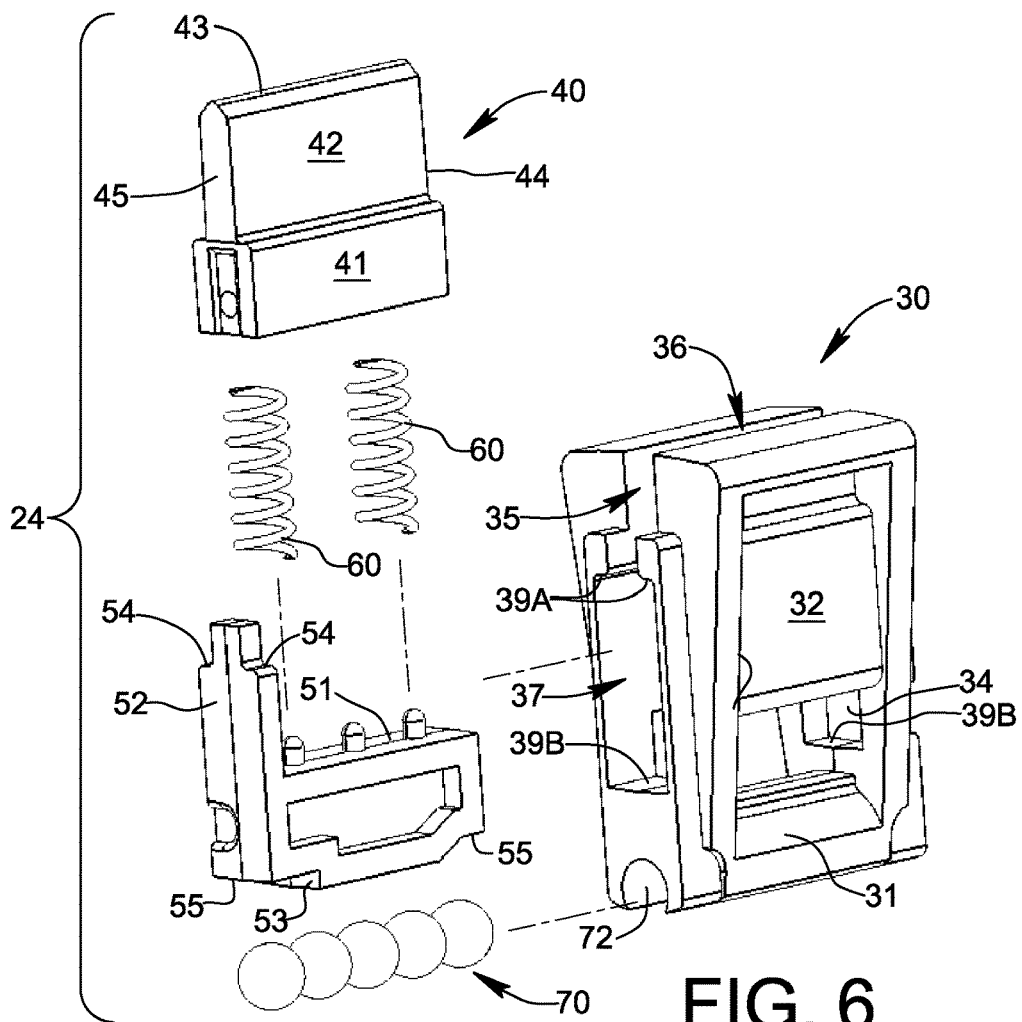
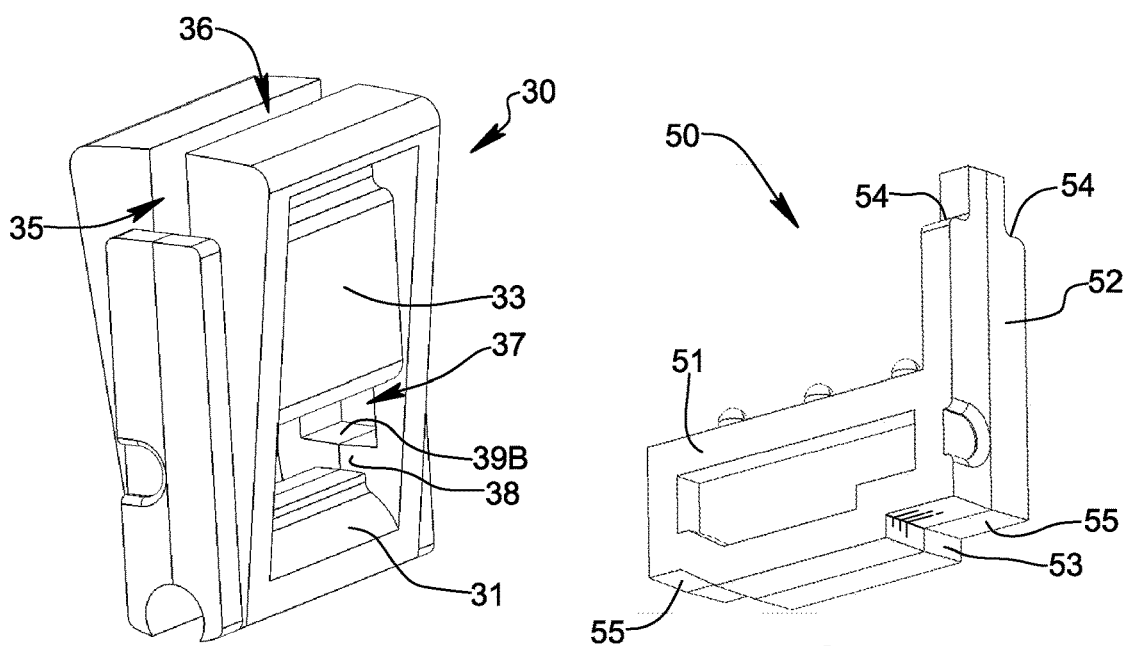
FIG. 6
FIG. 7
FIG. 8

PERISTALTIC PUMP HAVING IMPROVED PUMPING FINGERS

FIELD OF THE INVENTION

The present invention relates to pumping fingers for a peristaltic infusion pump for engaging tubing of an administration set loaded in the pump.

BACKGROUND OF THE INVENTION

Programmable infusion pumps are used to carry out controlled delivery of liquid food for enteral feeding and medications for various purposes such as pain management. In a common arrangement, an infusion pump receives a disposable administration set comprising flexible tubing having a resiliently deformable tubing segment designed to be engaged by a pumping mechanism of the infusion pump. For example, the pumping mechanism may include a plurality of fingers sequentially driven against the tubing segment to locally deform the tubing segment in a peristaltic manner to force liquid through the tubing toward the patient. During pumping, a platen member of the infusion pump is held at a fixed position on a side of the tubing segment opposite from the pumping mechanism to provide a platen surface along the tubing segment for keeping the tubing segment in place against the pressure of the pumping fingers.

In the Curlin 6000 curvilinear peristaltic infusion pump marketed by applicant, the pumping fingers are embodied as individual subassemblies designed to follow a cam surface of a motor-driven eccentric cam. As the cam rotates, the respective finger subassemblies are moved generally radially in sequential peristaltic fashion to engage and temporarily deform the tubing segment such that liquid is pumped through the tubing of the administration set in the direction of the patient. As shown in FIGS. 1 and 2, each pumping finger subassembly includes a housing having an inverted T-shaped slot extending in a transverse direction of the housing, a separate pinch member received in the inverted T-shaped slot of the housing, and a pair of springs for biasing the pinch member upward in the slot away from a base of the housing. The pinch member has a tip portion protruding upwardly from the housing into engagement with a tubing segment of the administration set. The housing has a leading wall, a trailing wall, and a first side wall cooperating with the base of the housing to define the inverted T-shaped slot. In order to permit the pumping finger subassembly to be assembled during manufacturing, a second side of the housing opposite the first side wall of the housing is open so that the pinch member and biasing springs may be inserted into the housing. The base of the housing includes a channel receiving roller bearings for engaging the cam surface.

As will be understood, the biasing force on the pinch member determines the pump's "dead head" pressure (i.e. the maximum fluid pressure the pump can develop if there is a flow blockage downstream from the pump). Variation in the dead head pressure may occur if the tubing segment moves or shifts laterally relative to the pinch members of the pumping fingers because the pinch members will tilt off-center, thus decreasing the dead head pressure. The decrease in dead head pressure can be addressed by using stronger biasing springs to compensate for the variation, but this solution would lead to an undesirable overdesign accompanied by higher material costs, increased power consumption, and lower battery life. Using stronger springs may also result in a dead head pressure which is too high and increases safety risks to the patient. For example, if dead head pressure is too high, it could lead to vein damage in the patient if a pressure sensor of the pump fails and an occlusion within the tubing suddenly clears under high pressure.

SUMMARY OF THE INVENTION

The present disclosure provides an improved pumping finger subassembly for use in an infusion pump having a peristaltic pumping mechanism for pumping fluid through a tubing segment of an administration set received by the infusion pump between the pumping mechanism and a platen surface of the pump. The pumping mechanism is operable to displace a plurality of the pumping finger subassemblies relative to a platen surface of the pump such that the pumping finger subassemblies reversibly deform the tubing segment in sequential fashion to pump fluid through the tubing segment.

In a disclosed embodiment, the pumping finger subassembly may comprise a housing including a base, a leading wall, a trailing wall, and a first side wall arranged with respect to one another to define a transverse slot, wherein the transverse slot is open through an upper opening of the housing opposite the base and through a second side opening of the housing opposite the first side wall. The pumping finger subassembly may also comprise a pinch member received by the housing though the second side opening. The pinch member may include a pedestal portion and a tip portion extending upwardly from the pedestal portion. The pumping finger subassembly may further comprise a block member received by the housing though the second side opening. The block member may include a foot portion and a side wall portion extending upwardly from the foot portion, wherein the side wall portion of the block member closes at least a portion of the second side opening of the housing. At least one spring may be arranged to act between the foot portion of the block member and the pedestal portion of the pinch member to bias the pinch member in a direction causing the tip portion of the pinch member to protrude from the housing through the upper opening of the housing. A plurality of ball bearings may be disposed in a socket formed in the base of the housing of the pumping finger subassembly for engaging a cam surface of the pumping mechanism.

When the various components of the pumping finger subassembly are assembled, the pinch member is supported on its first side by the first side wall of the housing, and on the second side by the side wall portion of the block member. As a result, the pinch member is prevented from tilting off-center, thereby maintaining a consistent dead head pressure.

BRIEF DESCRIPTION OF THE DRAWINGS

The nature and mode of operation of the present invention will now be more fully described in the following detailed description of the invention taken with the accompanying drawing figures, in which:

FIG. 6 is an exploded view of the pumping finger subassembly shown in FIGS. 4 and 5;

FIG. 7 is a perspective view of a housing of the pumping finger subassembly shown in FIGS. 4 and 5; and FIG. 8 is a perspective view of a block member of the pumping finger subassembly shown in FIGS. 4 and 5.

DETAILED DESCRIPTION OF THE INVENTION

Figure 1:
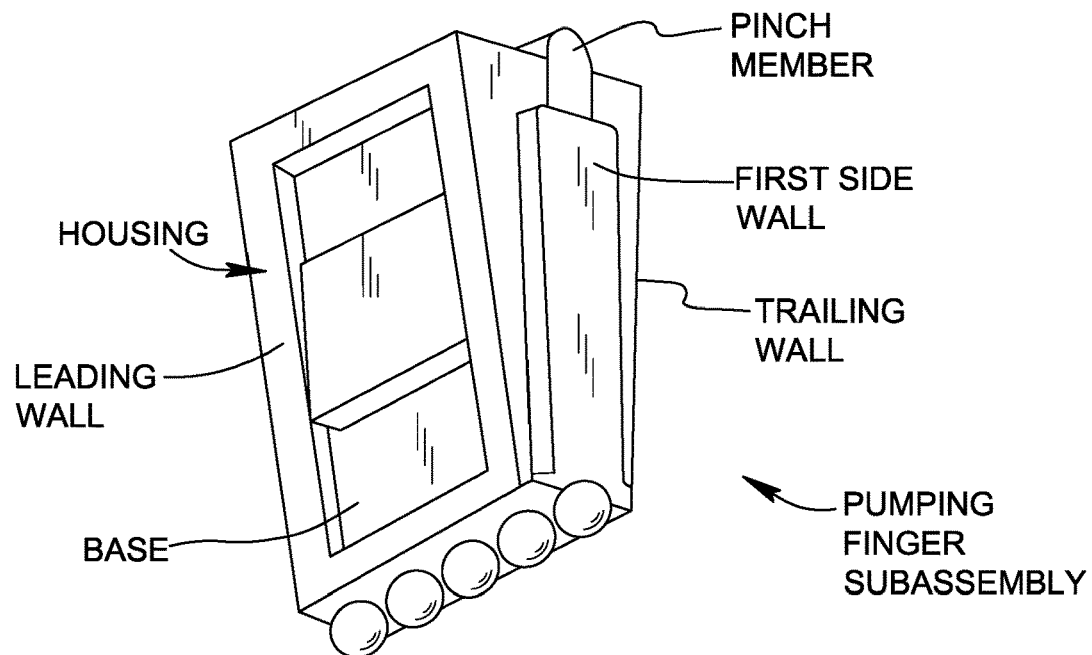
FIG. 1 is a perspective view showing a pumping finger assembly of the prior art.
Figure 2:
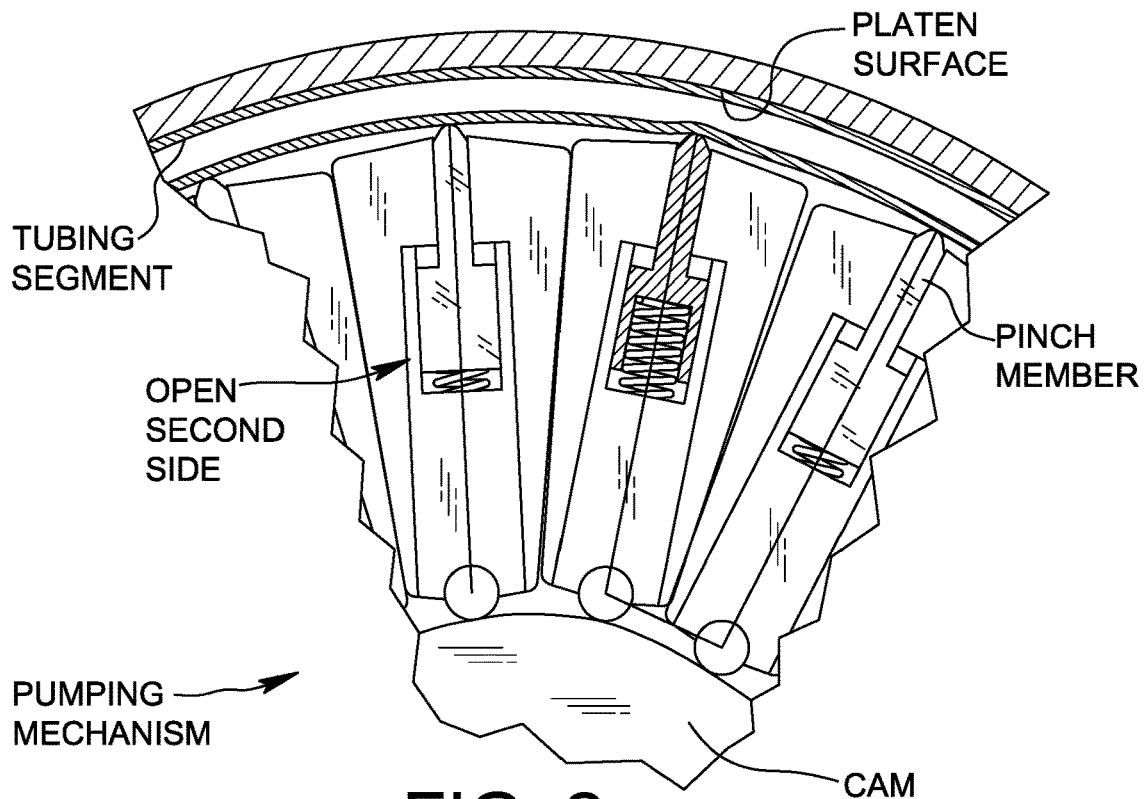
FIG. 2 is a side elevational view of the prior art pumping finger assembly shown in FIG. 1, showing a side of the pumping finger assembly opposite to the side visible in FIG. 1.
Figure 3:
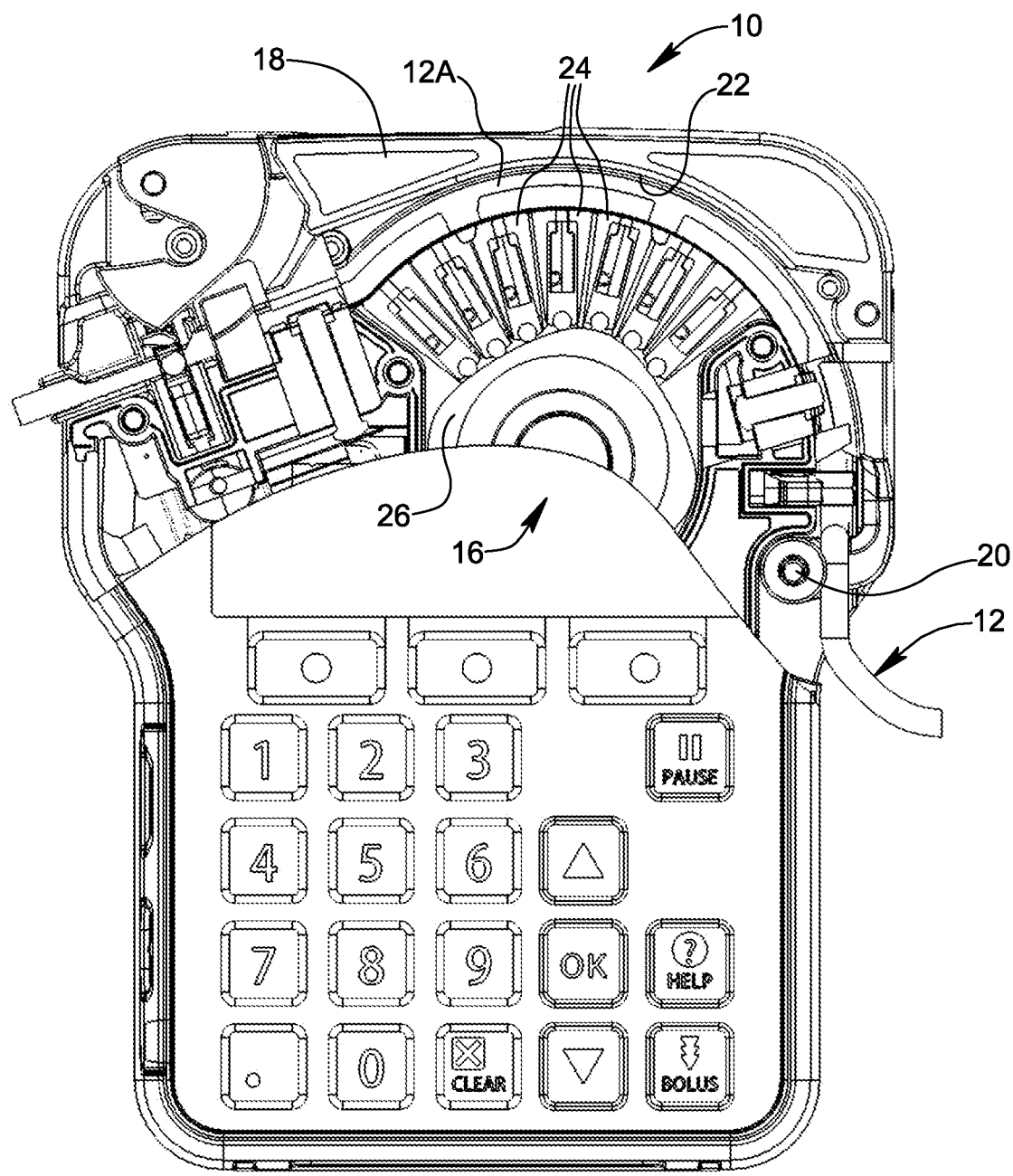
FIG. 3 is a front view of an infusion pump formed in accordance with an embodiment of the present invention, partially cutaway to show internal structure of the infusion pump, wherein an administration set is loaded in the infusion pump.

FIG. 3 shows an infusion pump 10 formed in accordance with a disclosed embodiment. Infusion pump 10 is shown with a disposable administration set 12 loaded in the pump, wherein administration set 12 is designed to be removably received by infusion pump 10. Administration set 12 includes flexible tubing acted upon by pump 10 to convey a flow of infusion liquid from a source reservoir (not shown) to a patient (not shown).

Infusion pump 10 comprises a pump body 14 including a pumping mechanism 16. Pump 10 also comprises a platen 18 rotatably coupled to pump body 14 to pivot relative to pump body 14 about the axis of a hinge pin 20. Platen 18 pivots between a closed position depicted in FIG. 3 in which a platen surface 22 of platen 18 is positioned opposite and in proximity to pumping mechanism 16 and an open position (not shown) in which the platen surface 22 is positioned away from pumping mechanism 16, thereby allowing a disposable administration set 12 to be loaded into infusion pump 10. When administration set 12 is loaded in pump 10 as shown in FIG. 3, a tubing segment 12A of the administration extends through pump 10 between pumping mechanism 16 on one side and platen surface 22 on the opposite side.

Pumping mechanism 16 is a peristaltic pumping mechanism having a plurality of pumping finger subassemblies 24 that are driven in sequential peristaltic fashion to engage and temporarily deform tubing segment 12A such that liquid is pumped through the tubing of administration set 12 in the direction of the patient. In the illustrated embodiment, pumping mechanism 16 has a curvilinear configuration, and pumping fingers 24 are moved generally radially by rotation of a motor-driven eccentric cam 26. Pumping mechanism 16 may take other forms, such as a linear peristaltic pumping mechanism having a plurality of axially spaced pumping finger subassemblies moved by respective cams mounted on a rotary shaft.

Figure 4:
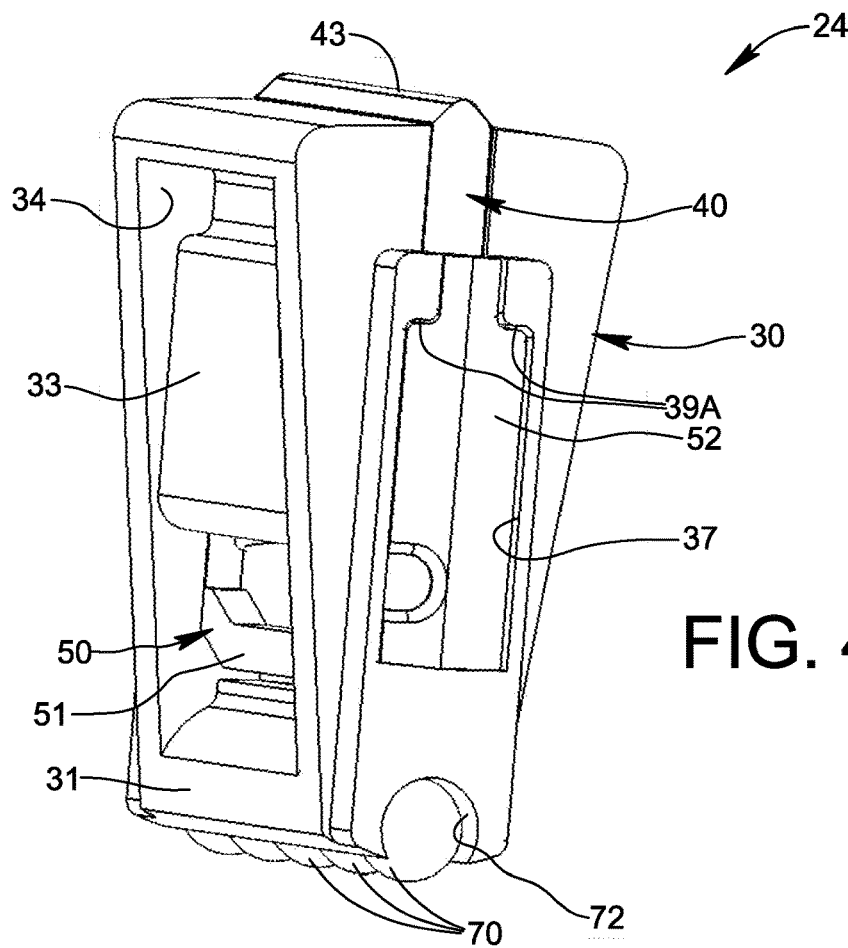
FIG. 4 is a perspective view of a pumping finger subassembly of the infusion pump shown in FIG. 3.
Figure 5:
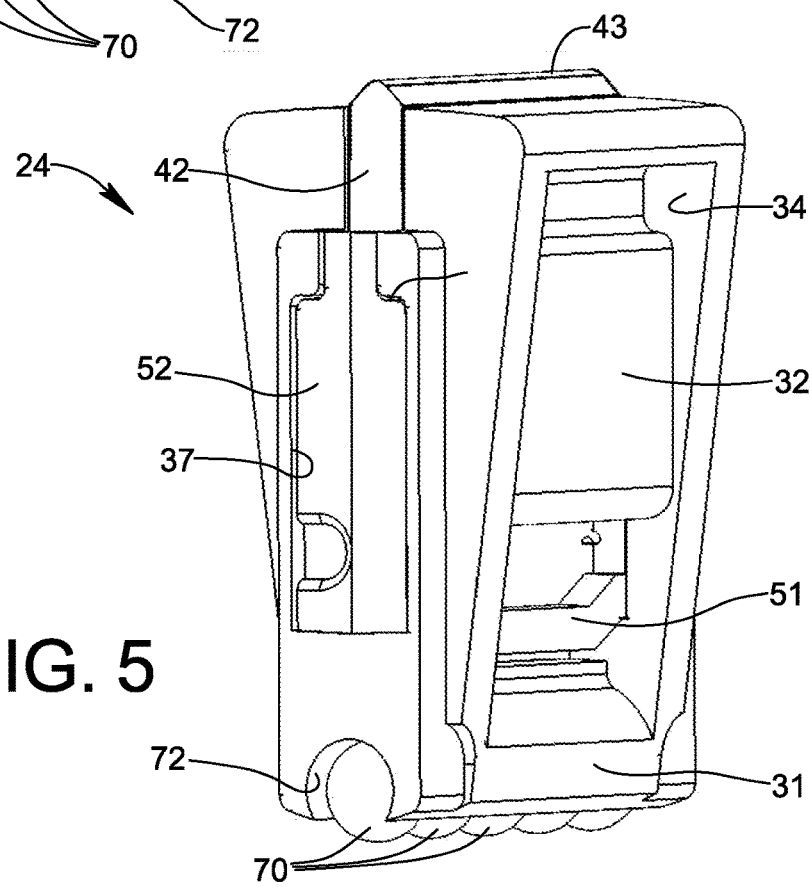
FIG. 5 is another perspective view of the pumping finger subassembly shown in FIG. 4.

A pumping finger subassembly 24 according to one embodiment is shown in FIGS. 4-6. Pumping finger subassembly 24 generally comprises a housing 30, a pinch member 40, a block member 50, and at least one spring 60.

Housing 30, shown in isolation in FIG. 7, includes a base 31, a leading wall 32, a trailing wall 33, and a first side wall 34 arranged with respect to one another to define a transverse slot 35. Transverse slot 35 is open through an upper opening 36 of housing 30 opposite base 31 and through a second side opening 37 of the housing opposite first side wall 34.

Pinch member 40 is received by housing 30 though second side opening 37. Pinch member 40 includes a pedestal portion 41 and a narrower tip portion 42 extending upwardly from pedestal portion 41. A distal end 43 of tip portion 42 may converge to form a rounded or blunt edge for engaging tubing segment 12A. Pinch member 40 includes a first side 44 and a second side 45 opposite first side 44.

Block member 50 is received by housing 30 though second side opening 37. Block member 50, shown in isolation in FIG. 8, includes a foot portion 51 and a side wall portion 52 extending upwardly from foot portion 51. As best seen in FIG. 4, side wall portion 52 may entirely close second side opening 37 of housing 30, or side wall portion 52 may be configured to close only a portion of second side opening 37.

One or more springs 60 are arranged to act between foot portion 51 of block member 50 and pedestal portion 41 of pinch member 40 to bias pinch member 40 in a direction causing tip portion 42 of pinch member 40 to protrude from housing 30 through upper opening 36, i.e. in a generally upward direction in the views of FIGS. 5 and 6. In accordance with the illustrated embodiment, a pair of coil springs 60 may be provided, one spring near each lateral side 44, 45 of pinch member 40, for laterally balanced biasing force. Alternatively, a single laterally-centered spring 60 may be used, or more than two springs 60 arranged in a laterally balanced manner may be used.

As will be understood, when the various components 30, 40, 50, and 60 are assembled to form pumping finger subassembly 24, pinch member 40 will be supported on first side 44 by first side wall 34 of housing 30, and on second side 45 by side wall portion 52 of block member 50.

Referring also to FIG. 8, block member 50 may include an external abutment surface 53 arranged to abut with an internal surface 38 of housing 30 adjacent to second side opening 37 to limit displacement of block member 50 relative to housing 30 in a lateral direction away from first side wall 34 of housing 30. Abutment surface 53 may be provided on foot portion 51 of block member 50.

Side wall portion 52 of block member 50 may include at least one upwardly facing shoulder 54 arranged to abut with a corresponding downwardly facing surface 39A of housing 30 to limit displacement of block member 50 relative to housing 30 in an upward direction away from base 31 of housing 30. Downwardly facing surface(s) 39A of housing 30 may border second side opening 37.

Block member 50 may include at least one downwardly facing surface 55 arranged to abut with a corresponding upwardly facing surface 39B of housing 30 to limit displacement of block member 50 relative to housing 30 in a downward direction toward base 31 of housing 30. In accordance with the illustrated embodiment, one downwardly facing surface 55 of block member 50 may be located on side wall portion 52 of the block member, and the corresponding upwardly facing surface 39B of housing 30 may border second side opening 37. Another downwardly facing surface 55 of block member 50 may be located at a distal end of foot portion 51, and the corresponding upwardly facing surface 39B of housing 30 may be an internal shelf adjacent first side wall 34.

A plurality of ball bearings 70 may be disposed in a cylindrical socket 72 formed in base 31 of housing 30 rollingly engaging a surface of cam 26. Ball bearings 70 may be, for example, nylon ball bearings.

Each of housing 30, pinch member 40, and block member 50 may be a monolithic part and may be formed of plastic by a suitable technique such as injection molding. Pumping finger subassembly 24 may be assembled by inserting pinch member 40 into housing 30 through second side opening 37, inserting springs 60 into housing 30 through second side opening 37 below a bottom surface of pedestal portion 41 of pinch member 40, and inserting foot portion 51 into housing 30 through second side opening 37 such that springs 60 engage the bottom surface of pedestal portion 41 and a top surface of foot portion 51. When foot portion 51 is fully received, block member 50 will snap into place and be constrained against movement as described above, whereby side wall portion 52 of block 50 will oppose first side wall 34 of housing 30 to provide bilateral support preventing pinch member 40 from tilting to either side. Ball bearings 70 may be press fitted into socket 72 to complete the assembly procedure.

While the present disclosure describes exemplary embodiments, the detailed description is not intended to limit the scope of the invention to the particular forms set forth. The invention is intended to cover such alternatives, modifications and equivalents of the described embodiments as may be included within the scope of the claims.

What is claimed is:

1. A pumping finger subassembly for a peristaltic infusion pump, the pumping finger subassembly comprising:
    a housing including a base, a leading wall, a trailing wall, and a first side wall arranged with respect to one another to define a transverse slot, wherein the transverse slot is open through an upper opening of the housing opposite the base and through a second side opening of the housing opposite the first side wall;
    a pinch member received by the housing though the second side opening, the pinch member including a pedestal portion and a tip portion extending upwardly from the pedestal portion;
    a block member received by the housing though the second side opening, the block member including a foot portion and a side wall portion extending upwardly from the foot portion, wherein the side wall portion of the block member closes at least a portion of the second side opening of the housing; and
    at least one spring arranged to act between the foot portion of the block member and the pedestal portion of the pinch member to bias the pinch member in a direction causing the tip portion of the pinch member to protrude from the housing through the upper opening of the housing;
    wherein the block member includes an external abutment surface arranged to abut with an internal surface of the housing adjacent to the second side opening to limit displacement of the block member relative to the housing in a lateral direction away from the first side wall of the housing.

2. The pumping finger subassembly according to claim 1, wherein the abutment surface is on the foot portion of the block member.

3. The pumping finger subassembly according to claim 1, wherein the side wall portion of the block member includes at least one upwardly facing shoulder arranged to abut with a downwardly facing surface of the housing to limit displacement of the block member relative to the housing in an upward direction away from the base of the housing.

4. The pumping finger subassembly according to claim 3, wherein the downwardly facing surface of the housing borders the second side opening.

5. An infusion pump operable to pump fluid through a tubing segment of an administration set received by the infusion pump, the infusion pump comprising:
    a plurality of pumping finger subassemblies according to claim 1;
    a platen surface opposite the plurality of pumping finger subassemblies, wherein the tubing segment is positioned between the plurality of pumping finger subassemblies and the platen surface when the administration set is loaded in the pump; and
    a pumping mechanism operable to displace the plurality of pumping finger subassemblies relative to the platen surface to reversibly deform the tubing segment to pump fluid through the tubing segment.

6. A pumping finger subassembly for a peristaltic infusion pump, the pumping finger subassembly comprising:
    a housing including a base, a leading wall, a trailing wall, and a first side wall arranged with respect to one another to define a transverse slot, wherein the transverse slot is open through an upper opening of the housing opposite the base and through a second side opening of the housing opposite the first side wall;
    a pinch member received by the housing though the second side opening, the pinch member including a pedestal portion and a tip portion extending upwardly from the pedestal portion;
    a block member received by the housing though the second side opening, the block member including a foot portion and a side wall portion extending upwardly from the foot portion, wherein the side wall portion of the block member closes at least a portion of the second side opening of the housing; and
    at least one spring arranged to act between the foot portion of the block member and the pedestal portion of the pinch member to bias the pinch member in a direction causing the tip portion of the pinch member to protrude from the housing through the upper opening of the housing,
    wherein the block member includes a downwardly facing surface arranged to abut with an upwardly facing surface of the housing to limit displacement of the block member relative to the housing in a downward direction toward the base of the housing.

7. The pumping finger subassembly according to claim 6, wherein the downwardly facing surface of the block member is on the side wall portion of the block member.

8. The pumping finger subassembly according to claim 6, wherein the upwardly facing surface of the housing borders the second side opening.

* * * * *